US00PP33381P2

(12) United States Plant Patent
Bernuetz

(10) Patent No.: US PP33,381 P2
(45) Date of Patent: Aug. 17, 2021

(54) ***SCAEVOLA* PLANT NAMED 'BONSCA 210'**

(50) Latin Name: *Scaevola aemula*
Varietal Denomination: Bonsca 210

(71) Applicant: Andrew Bernuetz, Silverdale (AU)

(72) Inventor: Andrew Bernuetz, Silverdale (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 17/013,754

(22) Filed: Sep. 7, 2020

(51) Int. Cl.
*A01H 5/02* (2018.01)
*A01H 6/00* (2018.01)

(52) U.S. Cl.
USPC ..... Plt./363

(58) Field of Classification Search
USPC ..... Plt./363
See application file for complete search history.

*Primary Examiner* — Susan McCormick Ewoldt
(74) *Attorney, Agent, or Firm* — C. Anne Whealy

(57) ABSTRACT

A new and distinct cultivar of *Scaevola* plant named 'Bonsca 210', characterized by its relatively compact and mounding plant habit; freely branching habit; early and freely flowering habit; long flowering period; flowers that are initially white in color becoming purplish pink in color with development; and good container and garden performance.

1 Drawing Sheet

Botanical designation: *Scaevola aemula.*
Cultivar denomination: 'BONSCA 210'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Scaevola* plant, botanically known as *Scaevola aemula* and hereinafter referred to by the name 'Bonsca 210'.

The new *Scaevola* plant a product of a planned breeding program conducted by the Inventor in Yellow Rock, New South Wales, Australia. The objective of the breeding program is to create new compact, mounding and early-flowering *Scaevola* plants with numerous attractive flowers.

The new *Scaevola* plant originated from an open-pollination in Yellow Rock, New South Wales, Australia in December, 2015 of a proprietary selection of *Scaevola aemula* identified by the code number 14-66, not patented, as the female, or seed, parent with an unknown proprietary selection of *Scaevola aemula*, as the male, or pollen, parent. The new *Scaevola* plant was discovered and selected by the Inventor as a single flowering plant from within the progeny of the stated open-pollination in a controlled greenhouse environment in Yellow Rock, New South Wales, Australia in December, 2016.

Asexual reproduction of the new *Scaevola* plant by vegetative tip cuttings in a controlled greenhouse environment in Yellow Rock, New South Wales, Australia since December, 2016 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bonsca 210'. These characteristics in combination distinguish 'Bonsca 210' as a new and distinct *Scaevola* plant:

1. Relatively compact and mounding plant habit.
2. Freely branching habit.
3. Early and freely flowering habit.
4. Long flowering period.
5. Flowers that are initially white in color becoming purplish pink in color with development.
6. Good container and garden performance.

Plants of the new *Scaevola* can be compared to plants of the female parent selection. Plants of the new *Scaevola* differ primarily from plants of the female parent selection in flower color as flowers of plants of the new *Scaevola* are initially white in color becoming purplish pink with development whereas flowers of plants of the female parent selection are initially white in color becoming blue with development.

Plants of the new *Scaevola* can be compared to plants of the *Scaevola aemula* 'Bonsca 1203', disclosed in U.S. Plant Pat. No. 27,511. In side-by-side comparisons, plants of the new *Scaevola* differ from plants of the 'Bonsca 1203' in the following characteristics:

1. Plants of the new *Scaevola* are more mounding than and not as trailing as plants of 'Bonsca 1203'.
2. Leaves of plants of the new *Scaevola* are oblanceolate in shape whereas leaves of plants of 'Bonsca 1203' are spatulate in shape.
3. Plants of the new *Scaevola* are more freely flowering than plants of 'Bonsca 1203'.
4. Plants of the new *Scaevola* and 'Bonsca 1203' differ in flower color as flowers of plants of the new *Scaevola* are initially white in color becoming purplish pink with development whereas flowers of plants of 'Bonsca 1203' are pink in color.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a side perspective view of a typical flowering plant of 'Bonsca 210' grown in a container.

The photograph at the bottom of the sheet is a close-up view of a typical flowering plant of 'Bonsca 210'.

DETAILED BOTANICAL DESCRIPTION

The aforementioned photographs and following observations, measurements and values describe plants grown during the late summer in 24-cm containers in an outdoor nursery in Higashiomi, Shiga, Japan and under cultural practices typical of commercial *Scaevola* production. During the production of the plants, day temperatures ranged from 15° C. to 30° C. and night temperatures ranged from 13° C. to 25° C. Plants were three months old when the photographs and the detailed description were taken. In the following description, color references are made to The Royal Horticultural Society Colour Chart, 2015 Edition, except where general tetms of ordinary dictionary significance are used.

Botanical classification: *Scaevola aemula* 'Bonsca 210'.

Parentage:

*Female, or seed, parent*.—Proprietary selection of *Scaevola aemula* identified as code number 14-66, not patented.

*Male or pollen parent*.—Unknown proprietary selection of *Scaevola aemula*, not patented.

Propagation:

*Type*.—By vegetative tip cuttings.

*Time to initiate roots, summer*.—About ten days at temperatures about 21° C. to 25° C.

*Time to initiate roots, winter*.—About 15 days at temperatures about 18° C. to 21° C.

*Time to develop roots, summer*.—About three weeks at temperatures about 21° C. to 25° C.

*Time to develop roots, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Relatively compact and mounding plant habit; moderately vigorous growth habit.

*Branching habit*.—Freely branching habit with lateral branches potentially forming at every node; pinching enhances branching potential.

*Plant height*.—About 38 cm.

*Plant diameter* (*area of spread*).—About 72 cm.

Lateral branch description:

*Length*.—About 28.3 cm.

*Diameter*.—About 1.7 mm.

*Internode length*.—About 1.9 cm.

*Aspect*.—Upright to outwardly.

*Texture*.—Sparsely pubescent; rough.

*Color*.—Close to 144A.

Leaf description:

*Arrangement*.—Alternate, simple; sessile.

*Length*.—About 4.2 cm.

*Width*.—About 1.9 cm.

*Shape*.—Oblanceolate.

*Apex*.—Acute.

*Base*.—Attenuate.

*Margin*.—Serrate.

*Texture, upper and lower surfaces*.—Pubescent; rough.

*Venation pattern*.—Pinnate, reticulate.

*Color*.—Developing leaves, upper surface: Close to NN137A. Developing leaves, lower surface: Close to 138A. Fully expanded leaves, upper surface: Close to 144A; venation, close to 137A. Fully expanded leaves, lower surface: Close to 144A; venation, close to 143A.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about 888 flowers per plant.

*Flowering time*.—Early flowering habit, plants begin flowering after about three to four weeks after planting; long flower period, plants flower continuously from spring into autumn in Japan.

*Flower longevity*.—Flowers typically last about a week on the plant; flowers not persistent.

*Fragrance*.—None detected.

*Flower buds*.—Length: About 1.4 cm. Diameter: About 2.6 mm. Shape: Lenticular. Color: Close to 148B; apex, close to 145A.

*Flowers*.—Diameter: About 1.3 cm by 2.2 cm. Depth: About 1 cm. Throat diameter: About 3.5 mm. Tube length: About 1.1 cm. Tube diameter, mid-section: About 3 mm. Tube diameter, proximally: About 1.7 mm.

*Petals*.—Quantity per flower: Five, fused at base. Length, beyond tube: About 1.2 cm. Width, beyond tube: About 4.8 mm. Shape: Narrowly elliptic. Apex: Cuspidate. Margin: Entire. Texture, upper and lower surfaces: Smooth, glabrous. Texture, throat: Pubescent. Texture, tube: Pubescent. Color: When opening, upper and lower surfaces: Close to NN155C. Fully opened, upper surface: Close to 68B; towards the base, close to NN155C; color does not change with development. Fully opened, lower surface: Close to 63C; midrib, close to N144D; color does not change with development. Throat, distally: Close to N144A. Throat, proximally: Close to 2A; venation, close to 183B. Tube: Close to N144A; venation, close to 186A.

*Sepals*.—Quantity per flower: Two. Length: About 5.5 mm. Width: About 1.5 mm. Shape: Lanceolate. Apex: Acute. Base: Fused. Margin: Entire. Texture, upper and lower surfaces: Pubescent. Color, upper and lower surfaces: Close to 137B.

*Reproductive organs*.—Androecium: Stamen quantity per flower: Five. Filament length: About 2 mm. Filament color: Close to 182A. Anther size: About 0.9 mm by 1.4 mm. Anther shape: Ellipsoidal. Anther color: Close to 10D. Pollen: Sparse. Pollen color: Close to 4D. Gynoecium: Pistil quantity per flower: One. Pistil length: About 9.4 mm. Style color: Close to 138D tinged with close to 187A; hairs, close to 187A. Stigma color: Close to 149D. Ovary color: Close to 138A.

*Seeds and fruits*.—To date, seed and fruit development have not been observed on plants of the new *Scaevola*.

Garden performance: Plants of the new *Scaevola* have been observed to have good garden performance and to tolerate rain, wind and temperatures ranging from about 0° C. to about 40° C.

Pathogen & pest resistance: To date, plants of the new *Scaevola* have not been shown to be resistant to pathogens and pests common to *Scaevola* plants.

It is claimed:

1. A new and distinct *Scaevola* plant named 'Bonsca 210' as illustrated and described.

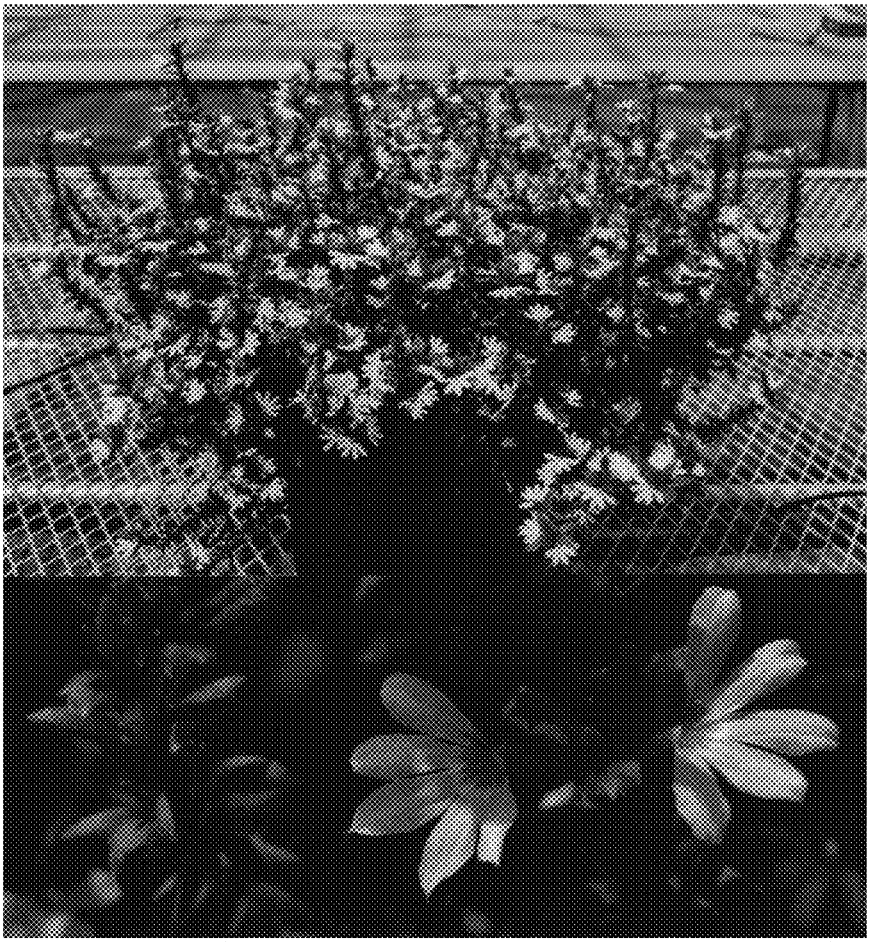

* * * * *